Figure 1:
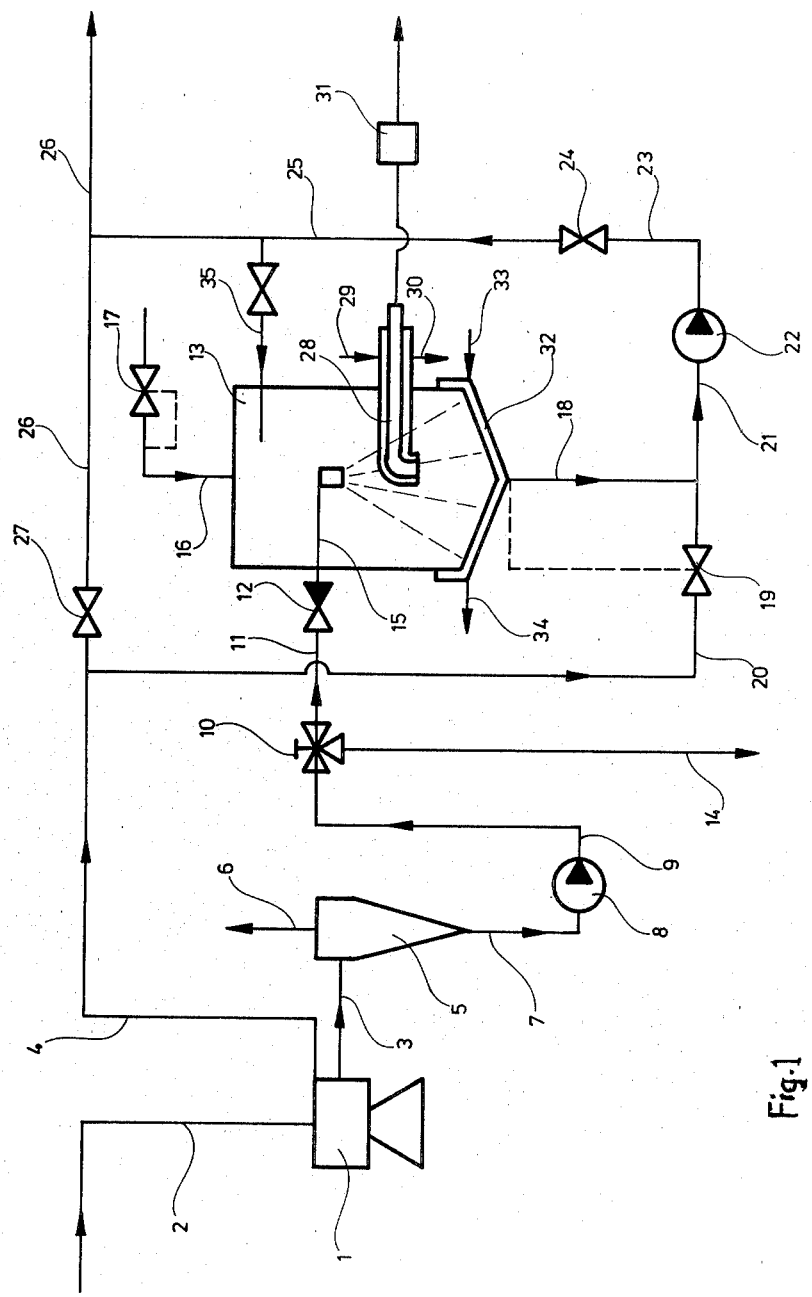

United States Patent [19]

Palm

[11] 4,390,350
[45] Jun. 28, 1983

[54] STERILIZATION OF BACTERIAL CONCENTRATES

[75] Inventor: Bengt A. Palm, Genarp, Sweden

[73] Assignee: Alfa-Laval AB, Tumba, Sweden

[21] Appl. No.: 420,910

[22] Filed: Sep. 21, 1982

[30] Foreign Application Priority Data

Sep. 22, 1981 [SE] Sweden ................................. 8105581

[51] Int. Cl.³ ...................... B01D 19/00; A23P 1/00; C12C 7/18
[52] U.S. Cl. .......................................... 55/38; 55/52; 55/202; 55/204; 55/206; 99/453; 422/26; 426/487; 426/491; 426/522
[58] Field of Search .................. 55/17, 38, 52, 54, 84, 55/86, 202, 204, 206, 208; 99/453, 455; 426/486, 487, 488, 491, 522; 422/26, 106, 292, 297

[56] References Cited

U.S. PATENT DOCUMENTS

| 2,428,044 | 9/1947 | Sharp | 426/487 |
| 2,634,907 | 4/1953 | Smith | 426/487 |
| 2,788,283 | 4/1957 | Stewart | 426/522 |
| 2,975,069 | 3/1961 | Laguilharre | 426/522 |
| 3,713,218 | 1/1973 | Laike | 99/453 |
| 3,973,048 | 8/1976 | Sollerud | 426/522 |
| 3,983,257 | 9/1976 | Malmberg | 426/491 |
| 4,310,476 | 1/1982 | Nahra | 426/521 |

Primary Examiner—Ernest G. Therkorn
Attorney, Agent, or Firm—Cyrus S. Hapgood

[57] ABSTRACT

In a process for sterilization of liquids like milk, containing gases such as air and carbon dioxide and microbes, a microbal enriched partial stream is separated by centrifugation and is degassed in a first step, whereupon the so treated partial stream is heated for sterilization and is then remixed with the rest of the original stream. The novelty is constituted by the manner of heating said partial stream, namely by injecting it in finely divided form into a closed container in which there is provided a steam atmosphere, the stream being discharged with level control from said container, whereas the remaining gas is separated and is discharged through an extra outlet.

10 Claims, 3 Drawing Figures

STERILIZATION OF BACTERIAL CONCENTRATES

This invention relates to a process and apparatus for treating streams of liquid containing gases like air and carbon dioxide and microbes, for example milk, in which a microbe-enriched partial stream is separated by centrifugation from said stream, which partial stream is subjected to a first degassing in order to remove most of the gases, whereupon said partial stream is sterilized through heating and is then remixed into said stream.

Such processes and corresponding apparatus have been in use for a long time, especially for sterilization of milk in connection with cheese production. The milk is centrifugated in a special nozzle centrifuge, a partial stream enriched in microbes, especially spores, being obtained from the incoming milk stream. This partial stream is then degassed in a special vacuum degasser in order to be nearly completely freed from any gases present, such as air and carbon dioxide. The degassing is necessary considering the subsequent sterilization step, which includes normally an injection nozzle in which a stream of live steam is caused to condense. It is not possible to achieve a stable condensation if the milk contains gases like air.

The process of sterilizing milk with an injection nozzle has been widely spread and is probably dominating in this field. Plants for carrying out this process show some drawbacks, however. They are sensitive to operational disturbances. A change of the capacity demands a change of the set flow-back pressure. The plants demand thorough cleaning with short time intervals. Due to the complicated design of the injection nozzles, automatic cleaning (so-called "cleaning-in-place") cannot be used, but manual cleaning must be carried out, which is expensive and time-consuming. Considering the prerequisite that gases must be removed more or less completely, to make the injection nozzle operate, expensive equipment is needed for such degassing.

Thus, there has for a long time been a demand for a simple method and apparatus of the type mentioned above, which will allow a variation of capacity without a troublesome set of the process parameters, and which will allow automatic cleaning of the used apparatus.

The principal object of the present invention is to provide a method and apparatus meeting such demand. The method is especially characterized in that said partial stream is fed through a dividing means into a closed container, whereby it is finely divided, steam also being introduced into said container for heating the partial stream by direct condensation. The partial stream is then discharged under level control through a first outlet from the container, while any gas remaining in said partial stream at the entrance into the dividing means, when finely dividing said stream, is separated from the liquid by a second degassing and is discharged through a second outlet from the container. When finely divided, liquid and remaining gas are separated so that the introduced steam can condense without disturbance in the particles obtained from the partial stream. Those particles fall towards the bottom of the container, where a constant liquid level is maintained by level control of a common type. The liberated gas is discharged through an outlet located above the bottom of the container.

In one embodiment of the process, the partial stream in said dividing means is given a helical flow path, so that liquid and remaining gas are separated by cyclone action.

The surface of the second outlet may be cooled, which surface is touched by the gas separated by the second degassing. Removal of separated gas from the container is thereby improved.

Apparatus for carrying out the process according to the invention comprises a centrifugal separator for separating an incoming stream into one main stream and one microbal-enriched partial stream, a cyclone separator for degassing and a closed container, the two last-mentioned parts being connected in series by lines arranged to convey said partial stream. The apparatus is characterized by an inlet to the container in the form of a dividing means designed to finely divide an incoming partial stream, the container also having a steam inlet, a first outlet for discharging the partial stream and located in the bottom of the container, a device for controlling the level of liquid in the container, and a second outlet for discharging gas. The first outlet is connected to a line for the main stream, so that the partial stream combined with the main stream constitutes the outgoing stream from the plant.

When the partial stream is finely divided by the dividing means in the container, liquid is separated from gases that are mixed therein. Particles of liquid constitute condensation nuclei for the steam, which raises their temperature to sterilization temperature. A certain holding time is obtained in the container due to the level control, which means that liquid of a certain amount is always present at the bottom of the container.

One suitable embodiment comprises a dividing means designed like an open container provided with a rotationally cylindrical wall and a gable with a tangential inlet, whereby an improved separation between liquid and gas is obtained.

It is especially advantageous to surround the second outlet for discharging gas with a cooling mantle, because in that case the separation of this gas from the container is facilitated. The outlet is connected to a thermodynamical gas- and condensate diverter of a design known per se, for automatic gas- and condensate discharge. It operates by discharging only gas which has a temperature lower than the temperature corresponding to saturated steam in the container. The bottom of the container may be provided with an outer cooling mantle, whereby the temperature of this part of the container can be limited so that the risk for deposits decreases.

Apparatus of the type just described is of simple design, allows stable operation with a simple possibility for variation of the capacity, and can easily be cleaned automatically, as it does not comprise any complicated parts. Furthermore, the apparatus has the advantage that it can be connected directly to a subsequent pasteurization step, which can completely make use of the heat fed (disregarding a minor quantity of heat which is cooled away in the cooling mantle of the second outlet and in the cooling mantle under the container).

BRIEF DESCRIPTION OF THE DRAWINGS

FIG. 1 shows a schematic view of the apparatus for carrying out the process according to the invention.

FIGS. 2 and 3 show the details of the injection nozzle.

The invention will now be described more in detail, reference being made to FIG. 1. In FIG. 1, a centrifugal separator 1 comprises a rotor provided with small nozzles in the periphery, there being an inlet line 2 for an incoming milk stream, an outlet line 3 for microbal enriched milk and an outlet line 4 for microbal exhausted milk 4. Line 3 is connected to a cyclone separator 5 with an outlet 6 for separated gas and an outlet 7 for degassed milk. Outlet 7 is connected to a closed container 13 which constitutes the so-called sterilization chamber, the connection being through a pump 8, a line 9, a two-way valve 10, a line 11 and a back valve 12. From the two-way valve 10 there is also a line 14 for a return stream. The container 13 is provided with an injection nozzle 15 which acts as a dividing means and gives the incoming stream a helical path. The container 13 is also provided with a steam inlet 16 through which the steam flow is controlled by a valve 17. In the bottom of the container 13 there is an outlet 18 with a level sensing float (not shown) which acts upon a valve 19. The latter in turn controls the flow of microbal exhausted milk through a line 20 in a way to be described below. The combined streams from line 20 and outlet 18 are conveyed via a line 21, a pump 22, a line 23, a valve 24 and a line 25 to a line 26, which is connected to the outlet line 4 for microbal exhausted milk. In line 26 there is a valve 27 downstream from the connection to line 20. In container 13 is a water mantled gas outlet line 28 below the injection nozzle 15. Cooling water is fed through an inlet 29 and is discharged through an outlet 30. The gas outlet line 28 is connected to a thermodynamical gas- and condensate diverter 31.

The bottom of the container 13 is provided with an outer mantle 32 to which cooling water is fed through an inlet 33, the water being discharged through an outlet 34. To clean the apparatus, container 13 has an inlet line 35 provided with a valve.

In the operation of the apparatus, milk is fed to the centrifugal separator 1 and a microbal enriched partial stream, about 2-3% of the incoming stream, is conveyed to the cyclone separator 5, where a large part of the air is separated and is discharged through the outlet 6. The stream, partly deaerated, is pumped into the container 13 through the injection nozzle 15, whereby the flow is finely divided and encounters steam, suitably of 135°-140° C., 2.2-2.7 bars, which is fed, pressure-controlled, through the steam inlet 16. The pressure is thus controlled by the valve 17. The stream, when flowing downwards from the injection nozzle, forms small droplets and acquires substantially the temperature of the steam by direct condensation. The level sensing float in the outlet 18 controls valve 19 so that the hot stream from the container 13, after a mean holding time of 5-15 seconds, is mixed with a stream of cold, microbal-exhausted milk from the outlet line 4 via the line 20 and the valve 19. The mixture is then recirculated by the pump 22 to the line 26, where the rest of the stream of microbal-exhausted milk from outlet 4 is flowing. The flow through valve 19 is preset by the valve 24, which is set in order that the temperature in line 21 will be a few degrees centigrade higher than that in the milk stream 2. If, for instance, the last-mentioned temperature is 64° C., the temperature in line 21 will be 68°-70° C. If the flow through container 13 should for some reason vary, the valve 19 will control the flow through line 20 so that the flow in line 21 will be substantially constant. The valve 27 serves to guarantee that the pressure in line 26 will not be higher than the stream pressure in the container 13 plus the pressure added by the pump 22.

Air and any other gas coming in with the microbal enriched stream to the container 13 is discharged through the gas outlet line 28, the entrance opening of which points downwards. A cold wall is formed on the pipe by the water mantle, which facilitates the separation of air and any other gas, which is discharged through the thermodynamical gas and condensate diverter 31.

The container is cooled by the outer mantle 32 below the bottom. The object is to prevent the stream in container 13 from hitting a bottom which is hotter than the stream. Any deposits are thereby avoided.

The valve 10 can be controlled by temperature sensing means (not shown) in container 13 in such a way that if the temperature is too low in the container, the valve is adjusted so that the microbal enriched stream is returned through the return line 14 until the temperature again is sufficiently high for sterilization.

Figure 2:
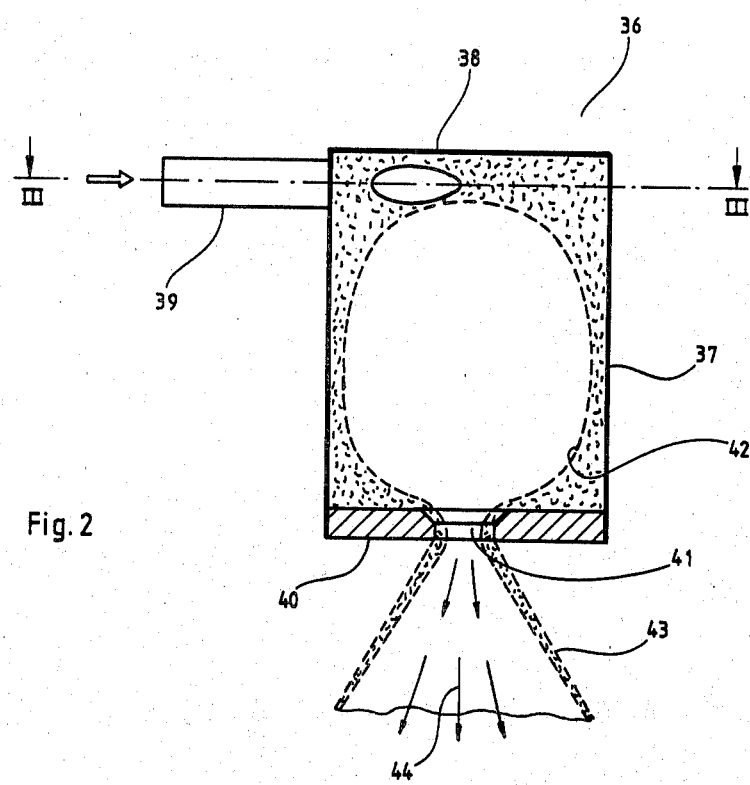
Figure 3:
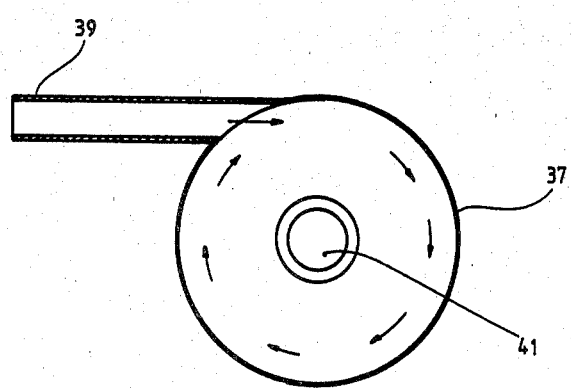

The injection nozzle 15 is described more in detail in FIGS. 2 and 3. It comprises a rotationally symmetrical container 36, with a wall 37. The container is provided with a closed gable 38 and a tangential inlet 39 in the vicinity of said gable 38. The container is also provided with another gable 40, in which there is a central opening 41. As the gable 40 is made from thick material, the opening 41 is formed like a nozzle, the cross section of which is in the direction outward.

In operation, the microbial enriched stream enters through inlet 39 and makes a swirling motion along the wall of container 36, so that there is formed a gas-liquid surface 42 in the container. The liquid is discharged through opening 41, forming a cone, indicated by reference number 43. Air and any other gas, which has been set free, is indicated by the arrows 44.

As modern food processes demand circulation cleaning without demontage and manual cleaning, the cleaning is intended to be carried out in the normal process path with alkali, water, etc. When the inlet line 35 is used for cleaning, the float in the outlet 18 will cause the flow through the valve 19 to decrease as much as the flow which goes through the inlet line 35. The back valve 12 will prevent steam from reaching the pump 8 if this should stop.

I claim:

1. In the treatment of a liquid containing gases, such as air and carbon dioxide, and microbes, the process which comprises subjecting a stream of said liquid to centrifuging to separate it into a microbe-enriched partial stream and a flow of microbal-exhausted liquid, subjecting said partial stream to a first degassing to remove most of the gases therefrom, then feeding said partial stream into a closed container by way of a step which finely divides the partial stream, introducing steam into said container to heat said partial stream by direct condensation of the steam, discharging a heated partial stream through a first outlet of said container while controlling the liquid level in the container, separating from the liquid in said container residual gas in said liquid, and discharging the separated residual gas through a second outlet from the container.

2. The process of claim 1, in which said finely dividing step directs the partial stream in a helical flow path.

3. The process of claim 1, which comprises also cooling the surface of said second outlet contacted by said residual gas.

4. The process of claim 1, comprising also combining the heated partial stream from said first outlet with a cold stream of said microbe-exhausted liquid.

5. The process of claim 4, comprising also maintaining a substantially constant relationship between the flow path rates of said two combined streams.

6. Apparatus for treating a liquid containing gases, such as air and carbon dioxide, and microbes, which comprises a centrifuge for separating an incoming flow of said liquid into a main stream and a microbal-enriched partial stream, a cyclone separator, means for conveying said partial stream from the centrifuge to the cyclone separator to degas the partial stream, a closed container, dividing means for receiving the partial stream from the cyclone separator and forming an inlet to the container, said dividing means being operable to deliver the partial stream in finely divided form into the container, said container having a stream inlet and also having a bottom outlet for discharging the partial stream and a second outlet for discharging gas separated from said stream in the container, and a device for controlling the level of liquid in the container.

7. The apparatus of claim 6, in which said dividing means is an injection nozzle.

8. The apparatus of claim 6, in which said dividing means includes an open container provided with a rotationally cylindrical wall having a gable with a tengential inlet for said partial stream.

9. The apparatus of claim 6, comprising also means including a mantle for circulating cooling fluid around said second outlet.

10. The apparatus of claim 6, comprising also means including a mantle for circulating cooling fluid at the bottom of the container.

* * * * *

UNITED STATES PATENT AND TRADEMARK OFFICE
CERTIFICATE OF CORRECTION

PATENT NO. : 4,390,350

DATED : June 28, 1983

INVENTOR(S) : Bengt A. Palm

It is certified that error appears in the above-identified patent and that said Letters Patent is hereby corrected as shown below:

Column 3, line 66, "stream" should read -- steam --.

Column 5, line 15, "stream" should read -- steam --.

Signed and Sealed this

First Day of May 1984

[SEAL]

Attest:

GERALD J. MOSSINGHOFF

Attesting Officer     Commissioner of Patents and Trademarks